(12) United States Patent
Price et al.

(10) Patent No.: US 10,668,080 B2
(45) Date of Patent: Jun. 2, 2020

(54) PHOSPHAPLATIN COMPOUNDS AS THERAPEUTIC AGENTS FOR TREATMENT OF BONE OR BLOOD CANCERS

(71) Applicant: Phosplatin Therapeutics LLC, New York, NY (US)

(72) Inventors: Matthew Price, New York, NY (US); Tyler Ames, Long Island City, NY (US)

(73) Assignee: Phosplatin Therapeutics LLC, New York, NY (US)

(*) Notice: Subject to any disclaimer, the term of this patent is extended or adjusted under 35 U.S.C. 154(b) by 0 days.

(21) Appl. No.: 16/475,170

(22) PCT Filed: Jan. 5, 2018

(86) PCT No.: PCT/US2018/012490
§ 371 (c)(1),
(2) Date: Jul. 1, 2019

(87) PCT Pub. No.: WO2018/129257
PCT Pub. Date: Jul. 12, 2018

(65) Prior Publication Data
US 2019/0328748 A1    Oct. 31, 2019

Related U.S. Application Data

(60) Provisional application No. 62/443,416, filed on Jan. 6, 2017.

(51) Int. Cl.
*A61K 31/555*    (2006.01)
*A61K 9/00*    (2006.01)

(52) U.S. Cl.
CPC .......... *A61K 31/555* (2013.01); *A61K 9/0019* (2013.01)

(58) Field of Classification Search
CPC ..................... A61K 31/555; A61K 9/0019
USPC ........................................... 514/185
See application file for complete search history.

(56) References Cited

U.S. PATENT DOCUMENTS

| | | |
|---|---|---|
| 2009/0042838 A1 | 2/2009 | Bose |
| 2013/0064902 A1 | 3/2013 | Bose |
| 2013/0165680 A1 | 6/2013 | Bose et al. |
| 2014/0024848 A1 | 1/2014 | Luke et al. |
| 2014/0243293 A1 | 8/2014 | Bose et al. |
| 2015/0231151 A1 | 8/2015 | Bose |

FOREIGN PATENT DOCUMENTS

WO    2005/000858 A2    1/2005

*Primary Examiner* — Yevgeny Valenrod
(74) *Attorney, Agent, or Firm* — Fox Rothschild LLP

(57) ABSTRACT

Use of (pyrophosphato)platinum(II) or (pyrophosphato)platinum(IV) complexes ("phosphaplatin compounds"), especially (R,R)-1,2-cyclohexanediamine-(dihydrogen pyrophosphato)platinum(II) (or "PT-112"), as therapeutic agents for treatment of bone and blood cancers, or cancers that metastasize to bones, and methods thereof, are disclosed.

15 Claims, 11 Drawing Sheets

Section plan 1      Section plan 2      Section plan 3

PHOSPHAPLATIN COMPOUNDS AS THERAPEUTIC AGENTS FOR TREATMENT OF BONE OR BLOOD CANCERS

CROSS REFERENCE TO RELATED APPLICATIONS

This application claims the benefit under 35 U.S.C. § 119(e) of U.S. Provisional Application No. 62/443,416, filed on Jan. 6, 2017, which is incorporated herein by reference in its entirety.

TECHNICAL FIELD OF THE INVENTION

This invention relates to use of phosphaplatin compounds as therapeutic agents for the treatment of bone or blood cancers and methods thereof.

BACKGROUND OF THE INVENTION

Bones are made up of osteoid (hard), cartilaginous (tough and flexible), and fibrous (threadlike) tissues, as well as elements of bone marrow. Bone cancer can start in any bone in the body and in any type of bone tissues. If discovered early, bone cancer could be treated by surgery to remove the tumor and the cancerous cells, which would be ideal especially if the tumor and cancerous cells have not spread and can be removed cleanly. More often the treatment needs a combination of surgery with other treatments, such as stem cell transplantation, chemotherapy, radiation therapy, etc. A targeted chemotherapy for the treatment of bone cancers, in principle, requires that the chemotherapy agent, after systemic administration, accumulate in the cancerous bone tissues. This requirement, in addition to the large variety of bone cancers, renders development of bone cancer therapies a challenging task.

Hematologic (or blood) cancer is a close relative to bone cancer since it begins in blood-forming tissue, such as the bone marrow, or in the cells of the immune system. Examples of hematologic cancer are leukemia, lymphoma, and multiple myeloma. In particular, multiple myeloma, a neoplastic plasma-cell disorder characterized by clonal proliferation of malignant plasma cells in the bone marrow microenvironment, monoclonal protein in the blood or urine, and associated organ dysfunction, accounts for approximately 1% of neoplastic diseases and 13% of hematologic cancers. (Palumbo, A. and Anderson, K.; "Multiple Myeloma," New. Engl. J. Med., 2011, 364(11): 1046-1060). Although treatments have been developed for multiple myeloma, including alkylating agents, glucocorticoids, immunomodulatory drugs (IMiDs), and proteasome inhibitors, see Chesi, M., et al., Blood, 2012, 120(2), 376-385, multiple myeloma is still considered a fatal B cell malignancy. US 2013/0281377A1.

The platinum-based antineoplastic agents, such as cisplatin, carboplatin, and oxaliplatin, though without an alkyl group, are sometimes described as "alkylating-like" due to their similar effects to those of alkylating antineoplastic agents. Cruet-Hennequart, S., et al. DNA Repair (Amst.), 2008, 7 (4): 582-596. They have been used for treating a variety of cancers, such as ovarian cancer, testicular cancer, small-cell lung cancer, and colorectal cancer.

A new class of platinum-based antitumor agents disclosed in U.S. Pat. Nos. 7,700,649 and 8,034,964, both to R. Bose, namely "phosphaplatin" complexes (because they contain a pyrophosphate group), function as anti-cancer agents without reliance on covalently binding DNA. As a result, they have been found to be efficacious in the treatment of various cisplatin and carboplatin-resistant cancers. These phosphaplatin compounds harbor a pyrophosphate moiety within their composition, which we posit may render these anti-cancer agents selective to targeting cancers that originate in, reside in, or metastasize to the bone.

Examples of such diseases include prostate or other solid tumor cancers that have a propensity to metastasize to bone, and multiple myeloma or other hematological malignancies that originate in bone.

SUMMARY OF THE INVENTION

This application discloses a method of treating a bone or blood cancer, or a cancer that metastasizes to bone, using phosphaplatin compounds, based on a surprising discovery that these pyrophosphato-platinum complexes can accumulate in bone tissues in treated mice and can effectively reduce M-spike levels in an established multiple myeloma mice model.

The method comprises, or consists essentially of, administering to a subject having a bone or blood cancer a therapeutically effective amount of a compound according to any one of formulae I to IV:

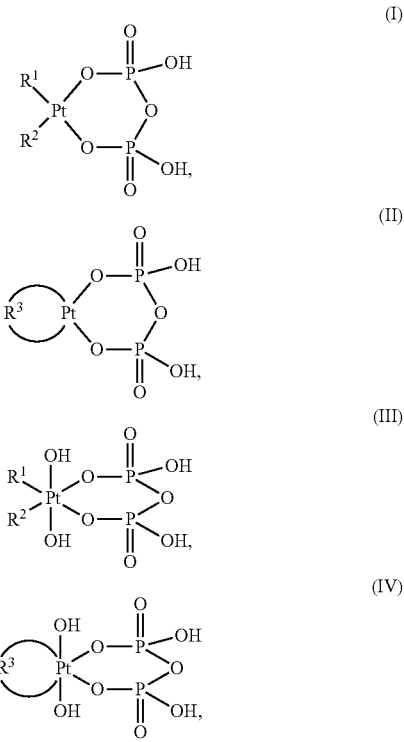

or a pharmaceutically acceptable salt or composition thereof, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

In some preferred embodiments, the phosphaplatin compound is 1,2-cyclohexanediamine-(dihydrogen pyrophosphato)platinum(II) ("pyrodach-2") having a structure of formula selected from the group consisting of:

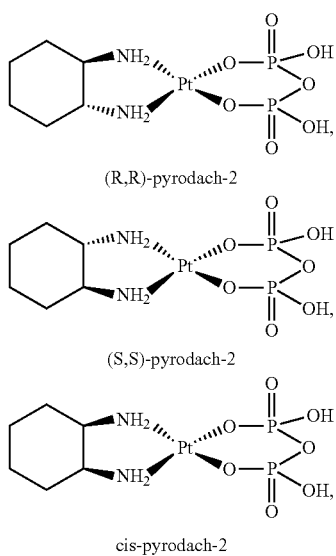

(R,R)-pyrodach-2

(S,S)-pyrodach-2 cis-pyrodach-2 which are, respectively, trans-(R,R)-1,2-cyclohexanediamine(pyrophosphato) platinum(II) ("(R,R)-pyrodach-2"), trans-(S,S)-1,2-cyclohexanediamine(pyrophosphato) platinum(II) ("(S,S)-pyrodach-2"), and cis-1,2-cyclohexanediamine (pyrophosphato) platinum(II) ("cis-pyrodach-2").

In another aspect, the present invention includes use of any of the phosphaplatin compounds disclosed herein, or a pharmaceutically acceptable salt thereof, in the manufacture of a medicament for treatment of a bone or blood cancer or a cancer that metastasizes to bones. Other aspects and advantages of the invention will be better appreciated in view of the following drawings, description, and claims.

DETAILED DESCRIPTION OF THE INVENTION

Figure 1:
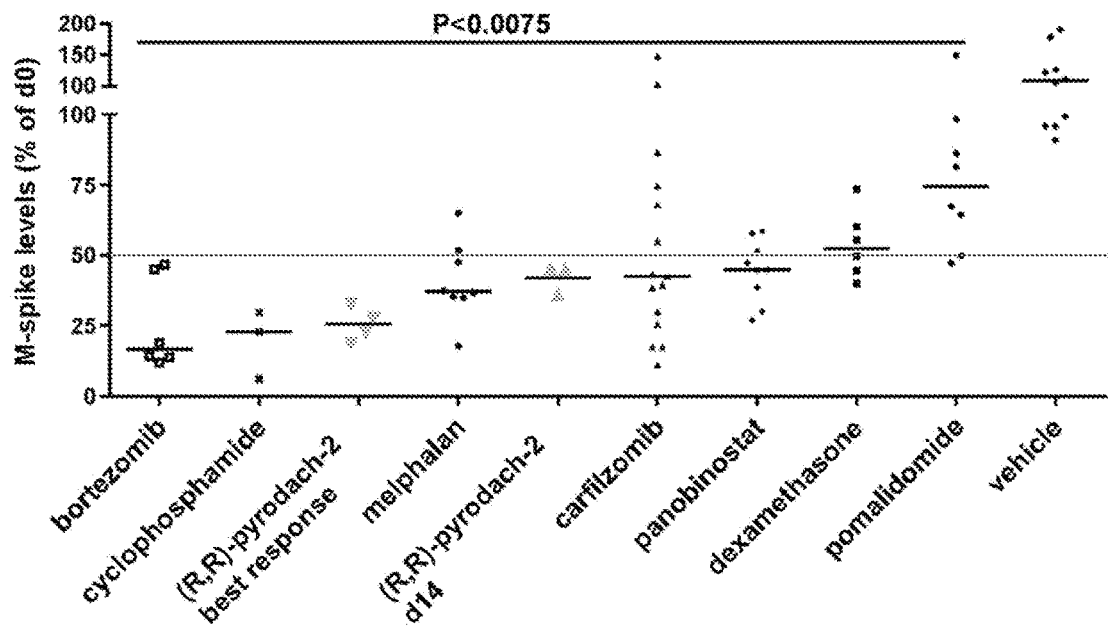
FIG. 1 illustrates the change of the M-spike levels in the transgenic Vk*Myc mice treated with (R,R)-pyrodach-2.

The present invention is based on the surprising discovery that phosphaplatin complexes administered to mice can accumulate in the bone tissues, among others, of the mice; and that the complexes can be used to effectively treat bone/blood cancers such as multiple myeloma as shown in the proven mice model, and to treat cancers that metastasize to bone tissues.

In one aspect, the present invention provides a method of treating bone or blood cancer in a subject, comprising administering to the subject a therapeutically effective amount of a phosphaplatin compound having a structure of formula I or II:

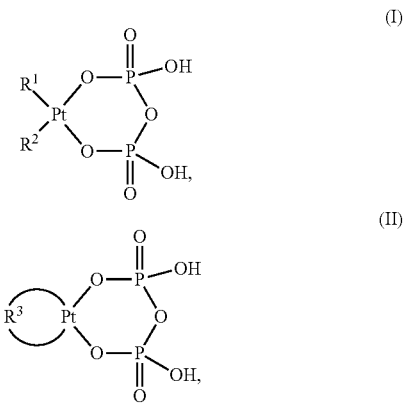

or a pharmaceutically acceptable salt thereof, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

The bone or blood cancer can be selected from osteosarcoma, chondrosarcoma, Ewing tumor, malignant fibrous histiocytoma (MFH), fibrosarcoma (fibroblastic sarcoma), giant cell tumor, chordoma, spindle cell sarcomas, multiple myeloma, non-Hodgkin lymphoma, Hodgkin lymphoma, leukemia, childhood acute myelogenous leukemia (AML), chronic myelomonocytic leukaemia (CMML), hairy cell leukaemia, juvenile myelomonocytic leukaemia (JMML), myelodysplastic syndromes, myelofibrosis, myeloproliferative neoplasms, polycythaemia vera, and thrombocythaemia, or the like.

In some embodiments, the bone or blood cancer is selected from osteosarcoma, chondrosarcoma, Ewing tumor, malignant fibrous histiocytoma (MFH), fibrosarcoma, giant cell tumor, chordoma, spindle cell sarcomas, multiple myeloma, non-Hodgkin lymphoma, Hodgkin lymphoma, leukemia, or the like. In one preferred embodiment, the bone or blood cancer is multiple myeloma.

In one embodiment of this aspect, $R^1$ and $R^2$ are each independently selected from $NH_3$, methyl amine, ethyl amine, propyl amine, isopropyl amine, cyclohexane amine, aniline, pyridine, and substituted pyridine; and $R^3$ is selected from 1,2-ethylenediamine and cyclohexane-1,2-diamine.

In another embodiment of this aspect, the phosphaplatin compound is selected from the group consisting of

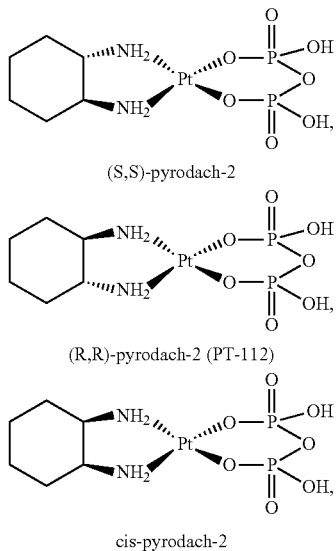

(S,S)-pyrodach-2

(R,R)-pyrodach-2 (PT-112)

cis-pyrodach-2 pharmaceutically acceptable salts, and mixtures thereof.

In a preferred embodiment, the phosphaplatin compound is R,R-pyrodach-2 having the formula:

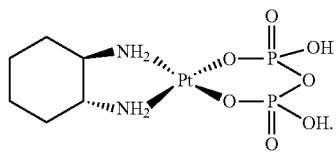

In one aspect, the present invention provides a method for treating a subject having a bone or blood cancer, comprising administering to the subject a therapeutically effective amount of a phosphaplatin compound having a structure of formula III or IV:

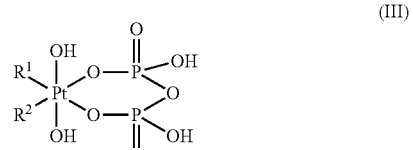

(III)

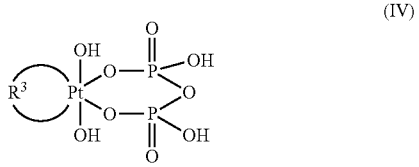

(IV)

or a pharmaceutically acceptable salt thereof, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

In one embodiment of this aspect, $R^1$ and $R^2$ are each independently selected from $NH_3$, methyl amine, ethyl amine, propyl amine, isopropyl amine, butyl amine, cyclohexane amine, aniline, pyridine, and substituted pyridine; and $R^3$ is selected from 1,2-ethylenediamine and cyclohexane-1,2-diamine.

In another embodiment of this aspect, the phosphaplatin compound has a formula (IV), wherein $R^3$ is 1,2-ethylenediamine or cyclohexane-1,2-diamine.

In another embodiment of this aspect, the phosphaplatin compound is selected from the group consisting of

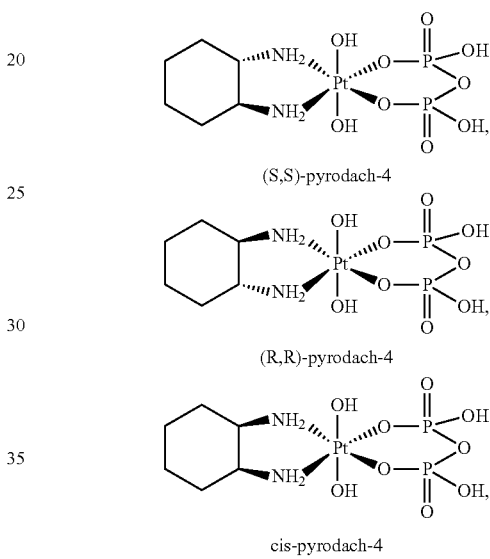

(S,S)-pyrodach-4

(R,R)-pyrodach-4 cis-pyrodach-4 pharmaceutically acceptable salts, and mixtures thereof.

In some embodiments, the administering comprises intravenous or intraperitoneal injection.

In some embodiments, the administering comprises intravenous injection.

In some embodiments, the administering comprises intraperitoneal injection.

In some embodiments, the dose of pyrophosphate platinum complex is in the range of from about 1 mg and to about 200 mg/Kg.

In some embodiments, the method is used in conjunction with administering to the subject a second anticancer agent.

In some embodiments, the second anticancer agent is selected from the group consisting of alkylating agents, glucocorticoids, immunomodulatory drugs (IMiDs) and proteasome inhibitors.

In another aspect, the present invention includes use of any of the phosphaplatin compounds disclosed herein, or a pharmaceutically acceptable salt thereof, in the manufacture of a medicament for treatment of a bone or blood cancer or a cancer that metastasizes to bones. In some embodiments, the phosphaplatin compound is selected from the group consisting of (R,R)-pyrodach-2, (S,S)-pyrodach-2, and cis-pyrodach-2. In some embodiments, the phosphaplatin compound is selected from the group consisting of (R,R)-pyrodach-4, (S,S)-pyrodach-4, and cis-pyrodach-4. In a preferred embodiment, the phosphaplatin compound is (R,R)-pyrodach-2 (or "PT-112").

The terminology used in the description of the invention herein is for describing particular embodiments only and is not intended to be limiting of the invention. As used herein, the singular forms "a," "an," and "the" are intended to include the plural forms as well, and vice versa, unless the context clearly indicates otherwise.

The term "about," as used herein, is intended to mean up to ±10% of an indicated value. Any ranges mentioned in the specification or the claims are to be understood as including the range itself and also anything subsumed therein, including both endpoints.

The term "subject" or "patient," as used herein, generally refers to a mammalian animal, including humans and animals such as dogs, cats, horses, and so on.

The term "composition," "pharmaceutical composition," or "pharmaceutically acceptable composition" means that a composition comprising a phosphaplatin compound and at least one pharmaceutically acceptable ingredient selected from carriers, diluents, adjuvants, and vehicles, which, as known in the art, generally refer to inert, non-toxic, solid or liquid fillers, diluents, or encapsulating materials unreactive with the phosphaplatin complexes.

The phosphaplatin compounds, pharmaceutical salts or complexes thereof, can be administered in a variety of ways, for example, orally, subcutaneously or parenterally including intravenous, intraarterial, intramuscular, intraperitoneally, intratonsillar, and intranasal administration as well as intrathecal and infusion techniques. A pharmacological formulation comprising the phosphaplatins containing any compatible carrier, such as various vehicles, adjuvants, additives, and diluents can be administered to the patient in an injectable formulation. See, e.g., WO 2017/176880, which is hereby incorporated by reference in its entirety. When administered parenterally, they generally will be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, or the like), suitable mixtures thereof, and vegetable oils. Sterile injectable solutions can be prepared by incorporating the phosphaplatin complexes in the required amount of the appropriate solvent with one or more of the other ingredients, as desired.

The disclosure is intended to cover any dosage of the phosphaplatin compounds that can cause therapeutic benefits on a subject having any bone or blood cancer, although the range of 1 to 200 mg/Kg based on a subject's body weight is disclosed to be generally preferred.

Bone or blood cancers that may be treated using the present invention include, without limitation, primary bone cancers such as various sarcomas, which start in the bone itself, secondary (or metastatic) bone cancers originated from other types of cancers, benign (noncancerous) bone tumors, and cancers that start in the blood forming cells of the bone marrow, which are also referred to as "blood cancers." Osteosarcoma (also called osteogenic sarcoma) is the most common primary bone cancer. This cancer starts in the bone cells and develops most often in bones of the arms, legs, or pelvis. Chondrosarcoma is a cancer of cartilage cells, which can develop anywhere there is cartilage, most often in bones such as the pelvis, leg bone or arm bone, occasionally in the trachea, larynx, and chest wall. Other sites are the scapula (shoulder blade), ribs, or skull. Chondrosarcoma has various type with distinctive features under a microscope. For example, dedifferentiated chondrosarcomas start out as typical chondrosarcomas but then some parts of the tumor change into cells like those of a high-grade sarcoma (such as high grade forms of malignant fibrous histiocytoma, osteosarcoma, or fibrosarcoma). Clear cell chondrosarcomas, which are rare, grow slowly and rarely spread to other parts of the body unless they have already come back several times in the original location. Mesenchymal chondrosarcomas can grow rapidly, but like Ewing tumor, are sensitive to treatment with radiation and chemotherapy.

Ewing tumor (also called Ewing sarcoma) is another common primary bone cancer, especially in children, adolescents, and young adults. Most Ewing tumors develop in bones, but they can start in other tissues and organs. The most common sites for this cancer are the pelvis, the chest wall (such as the ribs or shoulder blades), and the long bones of the legs or arms.

Malignant fibrous histiocytoma (MFH) often starts in soft tissue (connective tissues such as ligaments, tendons, fat, and muscle), also known as pleomorphic undifferentiated sarcoma. When MFH occurs in bones, it usually affects the legs (often around the knees) or arms. It mostly tends to grow locally, but can also spread to distant sites, such as lung.

Fibrosarcoma is another type of cancer that develops more often in soft tissues than in bones, often affecting bones in the legs, arms, and jaw.

Giant cell tumor of bone is a type of primary bone tumor that has benign and malignant forms, more often benign. Giant cell bone tumors typically affect the leg or arm bones of young and middle-aged adults and do not often spread to distant sites, but tend to come back where they started after surgery.

Chordoma is a primary tumor of bone that usually occurs in the base of the skull and bones of the spine and often does not spread to other parts of the body, but it often comes back in the same area if they are not removed completely. The lymph nodes, the lungs, and the liver are the most common areas for secondary tumor spread.

Spindle cell sarcomas are very similar to osteosarcomas but don't produce the bony substance called osteoid. There are several types of spindle cell sarcoma including undifferentiated sarcoma of bone, malignant fibrous histiocytoma, fibrosarcoma, and leiomyosarcoma.

Other kinds of cancers that are sometimes called "bone cancers" start in the blood forming cells of the bone marrow—not in the bone itself. The most common cancer that starts in the bone marrow and causes bone tumors is called multiple myeloma. Another cancer that starts in the bone marrow is leukemia, but it is generally considered a blood cancer rather than a bone cancer. Sometimes lymphomas, which more often start in lymph nodes, can start in bone marrow. Non-Hodgkin lymphoma generally develops in lymph nodes but sometimes starts in the bone. Hodgkin lymphoma develops in the lymphatic system from cells called lymphocytes, marked by the presence of an abnormal lymphocyte called the Reed-Sternberg cell (or B lymphocyte)

Benign (non-cancerous) tumors of cartilage are more common than malignant ones. These are called enchondromas. Another type of benign tumor that has cartilage is a bony projection capped by cartilage called an osteochondroma. These benign tumors rarely turn into cancer. There is a slightly higher chance of cancer developing in people who have many of these tumors, but this is still not common. Benign tumors do not spread to other tissues and organs and so are not usually life threatening. They are generally cured by surgery. Types of benign bone tumors include, but are not limited to, osteoid osteoma, osteoblastoma, osteochondroma, enchondroma, and chondromyxoid fibroma.

The method of treatment disclosed herein can also be used for other rare blood system cancers or disorders, for example, childhood acute myelogenous leukemia (AML), chronic myelomonocytic leukaemia (CMML), hairy cell leukaemia, juvenile myelomonocytic leukaemia (JMML), myelodysplastic syndromes, myelofibrosis, myeloproliferative neoplasms, polycythaemia vera, and thrombocythaemia.

The reference to "bone cancers" herein also includes metastatic lesions of solid tumor cancers, which are spread to the bones from somewhere else, such as breast cancer, prostate cancer, and lung cancer, in which populations the rates of these metastases are very high (estimated at 70%, 90% and 40% respectively in the metastatic populations). The cells of these types of cancers do not look or act like bone cancer cells, even though they are lesions in the bones. Since these cancer cells still act like the origin cancer cells, they usually still need to be treated with drugs that are used for the origin cancers. Since phosphaplatin complexes disclosed herein have proven to be effective therapeutic agents for various types of cancers as disclosed previously, see, e.g., U.S. Pat. Nos. 7,700,649 and 8,034,964, and US 2013/0064902A1, they can be used to treat or prevent metastatic bone cancers when used for treatment of all those other cancers. Therefore, the phrase "cancer that metastasizes to bone", as used herein, refers to any type of cancer, including but not limited to breast cancer, prostate cancer, and lung cancer, that has metastasized or spread to a bone structure.

In some embodiments, the method of the present invention may be preferably used in conjunction with other therapies, for example, stem cell transplantation, chemotherapy along with other anticancer drugs, and/or radiation therapy.

The following non-limiting examples further illustrate certain aspects of the present invention.

EXAMPLES

Example 1

Assay of R,R-pyrodach-2 Against Multiple Myeloma Cell Lines

The compound trans-(R,R)-1,2-cyclohexanediamine-(dihydrogen pyrophosphato) platinum(II) ("R,R-pyrodach-2") was tested on two multiple myeloma cell lines RPMI 8226 and MM1R. The IC50 values of R,R-pyrodach-2 against cell lines RPMI 8226 and MM1R were found to be 2.90 uM and 2.78 uM, respectively, which demonstrate the potency and activity of the compound.

Example 2

Test of R,R-pyrodach-2 on the Multiple Myeloma Mouse Model

Background

The trans-pyrodach-2 compound is tested on the multiple myeloma mouse model, in particular Vk*MYC mice, which has been reported to be a faithful preclinical model that predicts the clinical activity of drugs in untreated and relapsed MM (Chesi, M., et al., *Cancer Cell,* 2008, 23, 167-180; Chesi, M., et al., *Blood,* 2012, 120(2): 376-385). Additionally, the trans-pyrodach-2 compound was tested in mice engrafted with the more aggressive bortezomib resistant Vk12598, and in the multidrug resistant Vk12653 lines, both of which were generated from Vk*MYC mice.

Materials and Methods

De novo Vk*MYC mice were aged to one year or longer, and M-spike levels were monitored. After the concentrations of the predominant M-spike reached levels of between about 10 and 70 g/L (estimated by densitometry, comparing M-spike to albumin), mice were candidates for starting drug treatment. Mice brought onto the study were dosed either twice weekly (n=2) or thrice (n=1) weekly at a concentration of 100 or 67 mg/kg (R,R)-pyrodach-2, respectively, administered via IP injection after preparation in a phosphate buffer solution. M-spike levels were measured weekly, and post-treatment measurements were compared and normalized to the pre-treatment baseline measurement. Dosing was halted after two weeks of treatment.

Additionally, mice were engrafted with the Vk12598 transplantable line and received vehicle (n=11) or (R,R)-pyrodach-2 at a concentration of 62.5 mg/kg (n=12). Mice engrafted with the Vk12653 transplantable line were likewise treated with vehicle (n=10) or (R,R)-pyrodach-2 at 62.5 mg/kg (n=10). Both Vk12598 and Vk12653 engrafted mice were treated twice a week for two weeks via IP injection and monitored via survival and M-spike levels, respectively.

Results

The results from the de novo Vk*MYC mice are shown in FIG. 1, which illustrates treatment with (R,R)-pyrodach-2 resulted in >50% reductions in M-spike at the 2-week time point, passing the statistically correlated activity threshold indicative of robust activity in human MM patients for agents tested in the model. At this point treatment was discontinued, and M-spike levels continued to decline for 1-2 weeks (see "PT-112 best response" in FIG. 1), with the lowest observed M-spike at 19% of baseline 11 days after treatment discontinuation. These results were comparable or superior to those generated by treatment with approved MM SoC agents.

Figures 2A, 2B:
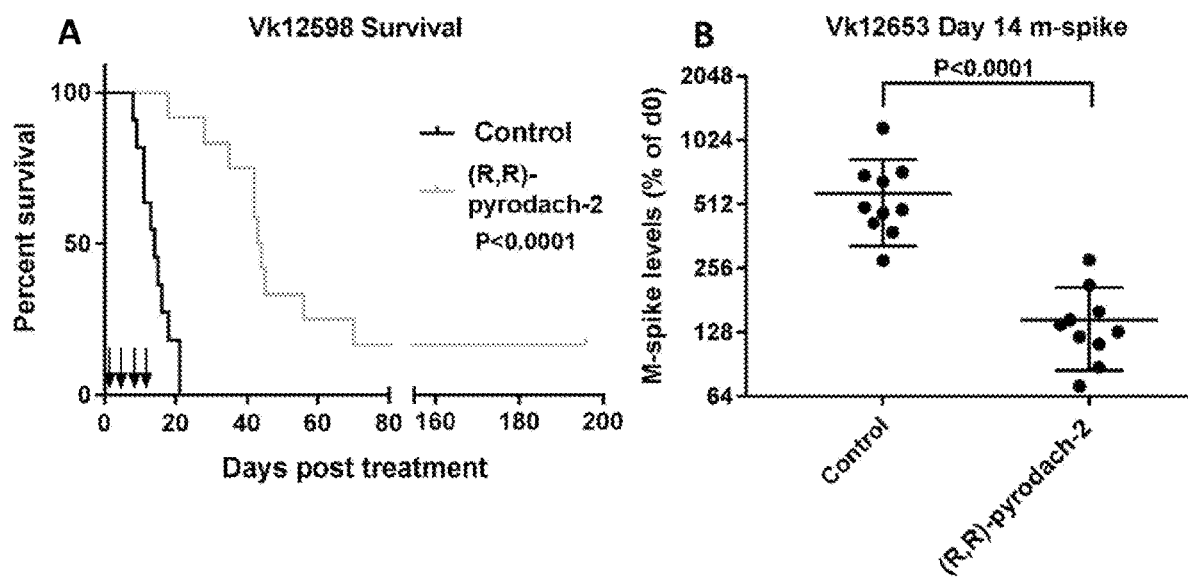
FIGS. 2A and 2B illustrate changes in (A) survival and (B) M-spikes levels in mice treated with (R,R)-pyrodach-2.

FIG. 2 shows results from Vk12598-engrafted (A) and Vk12653-engrafted (B) mice. In the case of the Vk12598-engrafted mice, treatment with (R,R)-pyrodach-2 resulted in significant increases in survival and a number of durable, complete response lasting over six months versus the vehicle control group, where all mice died by 21 days. Additionally, (R,R)-pyrodach-2 treatment caused a statistically significant reduction in M-spike levels in comparison to the vehicle control group in Vk12653-engrafted mice.

Conclusions (R,R)-Pyrodach-2 was well tolerated in the Vk*MYC mouse model when given twice or thrice weekly. Both doses were effective in reducing M-spike levels below 50% after two weeks of treatment. Additionally (R,R)-Pyrodach-2 treatment was active in both Vk12598 and Vk12653 mice, as indicated by increased survival and repression of M-spike level elevations, respectively. Taken together, and given the previous work in this model demonstrating the correlation between activity in the Vk*MYC model and clinical activity in human patients, these data suggest (R,R)-pyrodach-2 would be effective in treating human patients with multiple myeloma.

Example 3

Assay of Distribution of Platinum in R,R-pyrodach-2 Treated Mice

Materials and Methods

Five CD-1 mice were dosed with (R,R)-pyrodach-2, intravenous (IV), at a concentration of 90 mg/kg, and one additional mouse was dosed with vehicle (phosphate buffer). After dosing, the (R,R)-pyrodach-2 treated mice were euthanized at different time points (45 min, 3 hr, 12 hr, 24 hr, and 72 hr), and the control mouse was euthanized at 45 minutes post dosing. Subsequently, carcasses were snap frozen at −70° C. Slides of full body sagittal plane cross sections were prepared for the control, 45 min, and 24 hr mice. Laser Ablation Inductively Coupled Plasma Mass Spectrometry (LA-ICP-MS) was then used to scan the slides for the concentration of Pt (an atomic component of (R,R)-pyrodach-2) across the entire full body cross sections. Additional slides were prepared from adjacent positions and hematoxylin & eosin (H&E) stained to map the Pt signal to different organs and tissues.

Results

Figure 3:
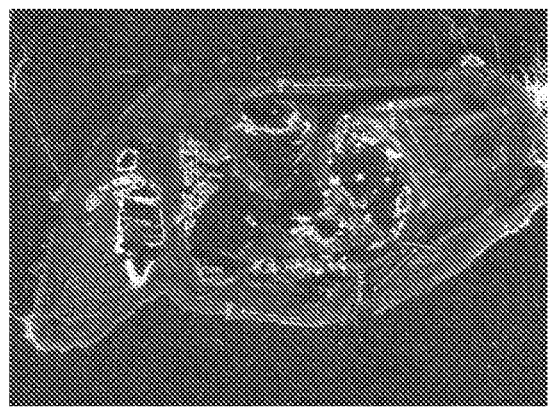
FIG. 3 illustrated ICP-MS imaging of screened regions (white bars) of mice treated with (R,R)-pyrodach-2 after 24 hrs.
Figure 4:
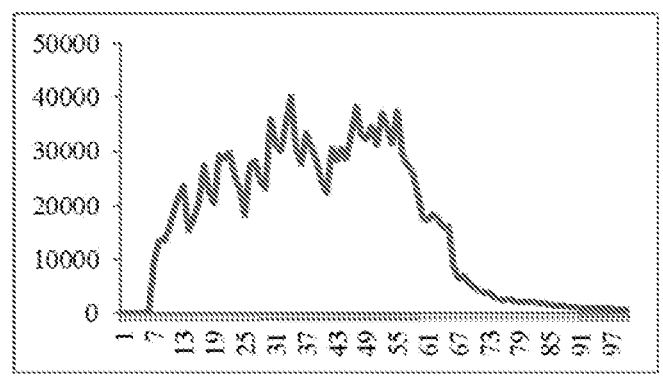
FIG. 4 illustrates detection of platinum in liver in treated mice at T24 h (raw data).

Good detection of Pt in tissue sections mounted onto indium tin oxide (ITO) slides into the treated sections at T45 min and T24 h was observed (Table 1). The LA-ICP-MS image of screened regions (white bars) of mice treated with (R,R)-pyrodach-2 after 24 hrs is shown in FIG. 3, and the detection of the Platinum in treated Liver T24 h (raw data) is shown in FIG. 4.

TABLE 1

Detection of the Platinum in organs (in counts, not present if blank)

| Organ | Control 45 min | Treated 45 min | Treated 24 h |
|---|---|---|---|
| Kidney |  | 345000 |  |
| Liver | 2 | 360000 | 28000 |
| Fat | 1 | 49000 |  |
| Intestines |  | 21000 | 26000 |
| Skin | 3.8 | 81000 | 32000 |
| Stomach | 1400 | 5000 | 4400 |

Conclusion

Good detection of the Pt was observed in both treated tissues in the different organs above limit-of-detection and limit-of-quantification as defined in the IUPAC gold book with k=3 and k=10, respectively.

Pt levels in every organ of the control animals are below the Pt levels in the corresponding organs in the exposed animals at statistically significant levels.

LA-ICP-MS Imaging

Objective

To detect the Platinum element (Pt) by LA-ICP-MS imaging into mouse whole-body sections at 150 μm spatial resolution covering the entire sections in the different section planes for the animals: Treated 45 min, Treated 24 h and Control 45 min (3 sectioning levels per animal).

Protocol

Figure 5:
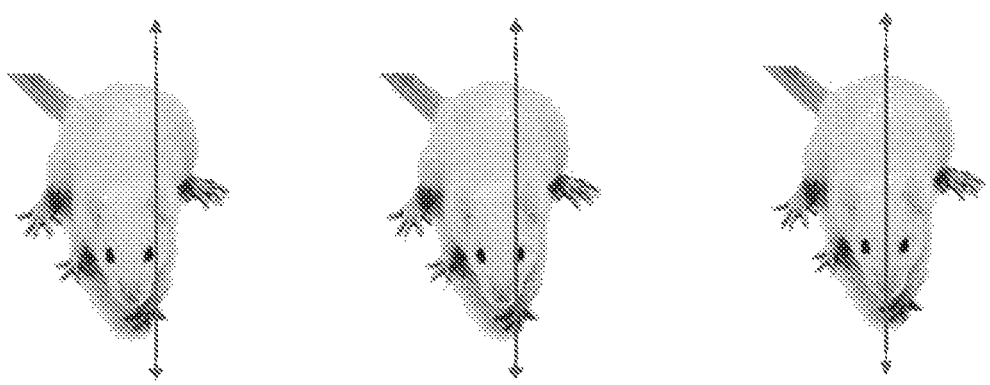
FIG. 5 illustrates three section plans on the treated mice for ICP-MS imaging for detection of platinum in the mice.

The mice were sectioned at 20 μm thickness in 3 different section planes with a cryostat and mounted onto ITO glass slides. See FIG. 5.

Level 1: sagittal section plane going through the left side of the left eye of the mouse Level 2: $2^{nd}$ sagittal plane at the right side of the left eye passing through a maximum of major organs.

Level 3: $3^{rd}$ sectioning level in the sagittal midline plane of the animal.

The regions of interest were defined as:

Priority level 1: bones (spine, pelvis, ribs, femur), liver, kidney.

Priority level 2: lung, spleen, heart, brain, thyroid, thymus.

The slides were cryo-desiccated for 30 min then stored at −80° C. until further use. The slides were dried under vacuum for 30 min at room temperature before ICP-MS imaging. Higher resolution images were also collected, focusing on bone-containing regions.

Analysis

Analyses were performed by LA-ICP-MS 2D for the tissue sections.

Results

Figure 6:
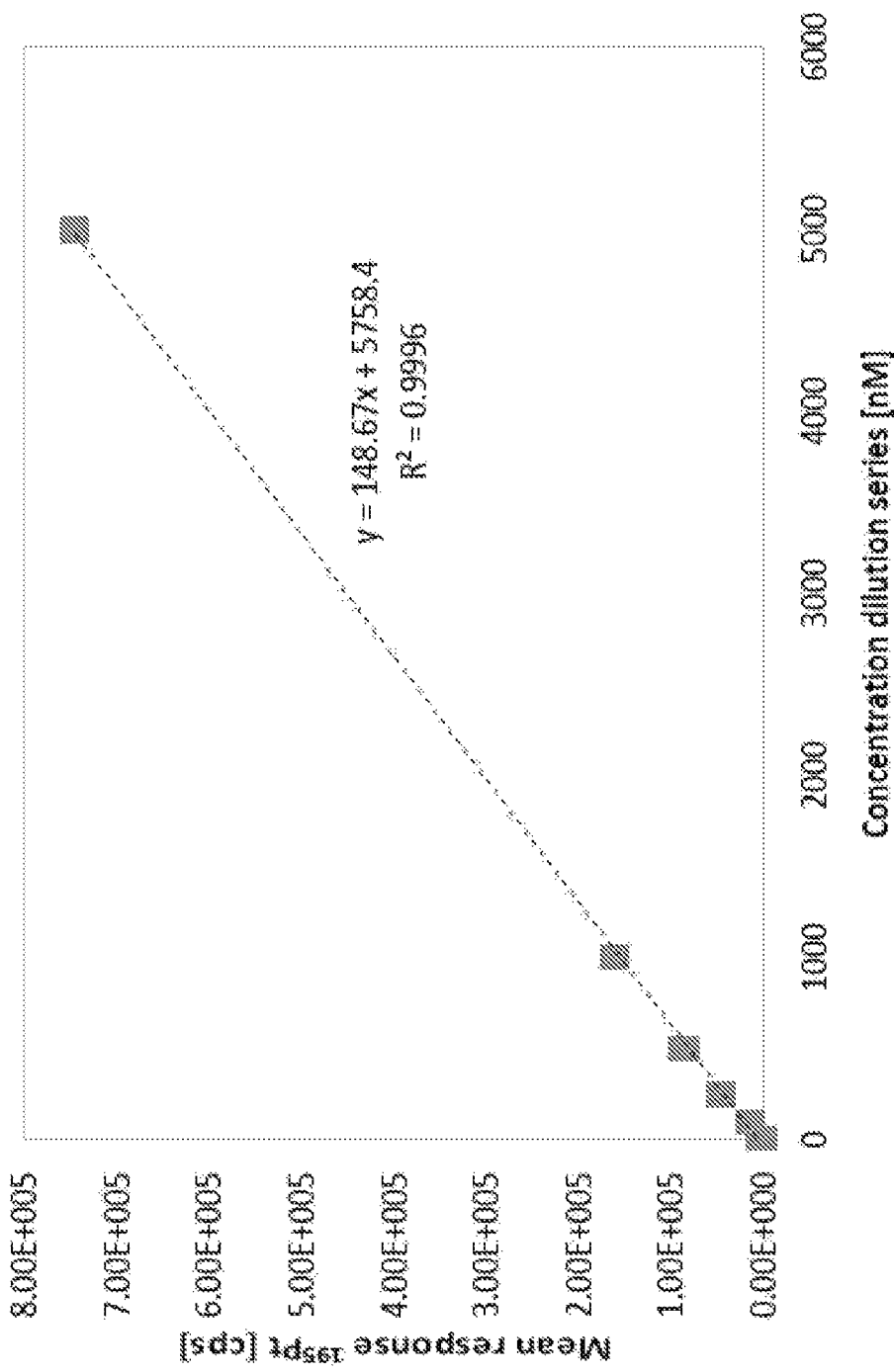
FIG. 6 illustrates the good linearity of the Pt by spotting the calibration standard onto liver control tissue sections.

Calibration was performed in the 10-5000 nM concentration range with 6 non-zero concentrations minimum to build the calibration curve. Good linearity of the Pt by spotting the calibration standard onto liver control tissue sections was observed (FIG. 6).

Figure 7:
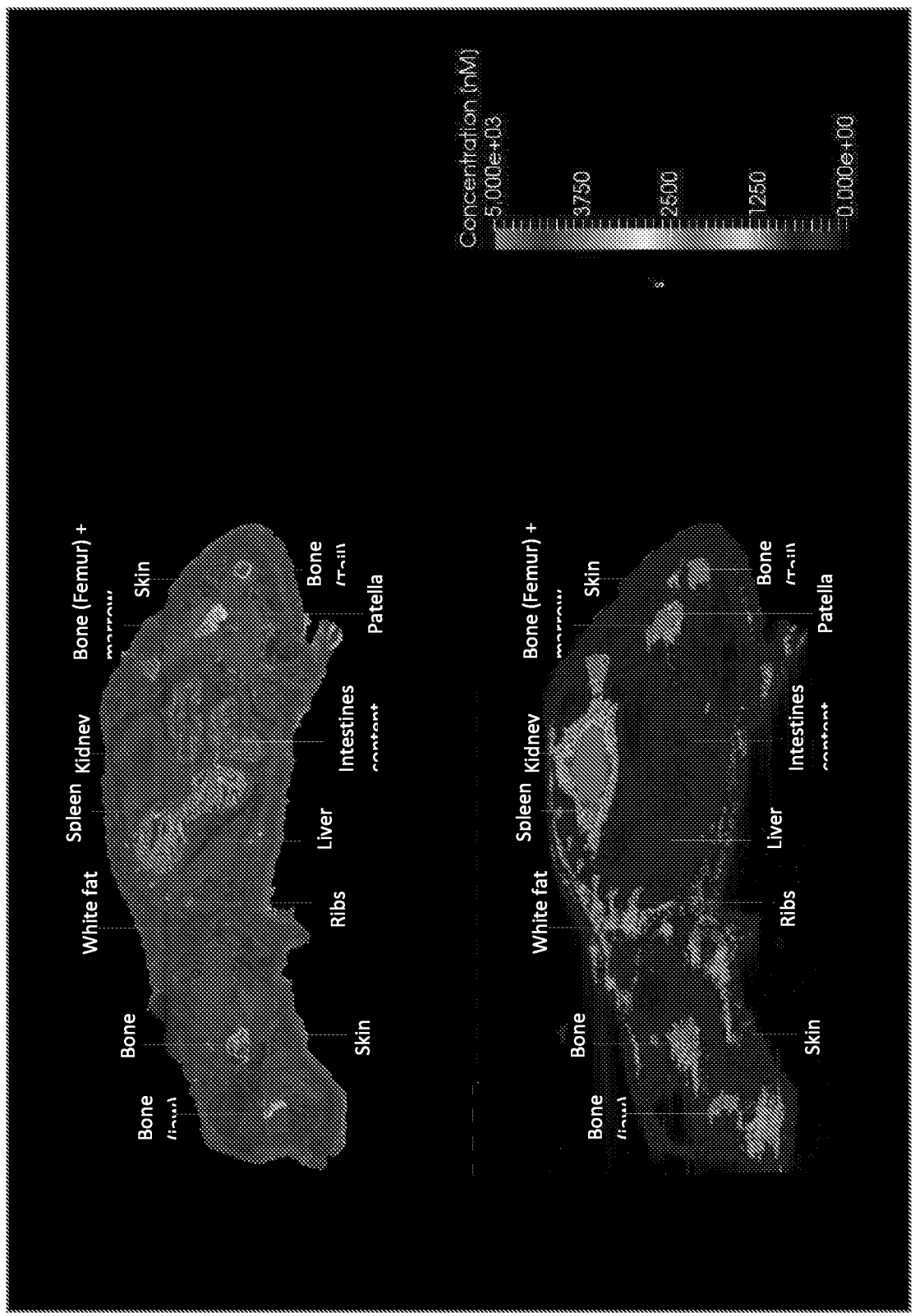
FIG. 7 shows the quantification imaging map based on the LA-ICP-MS analysis of platinum in treated mice at T45 min Section Plan 1.
Figure 8:
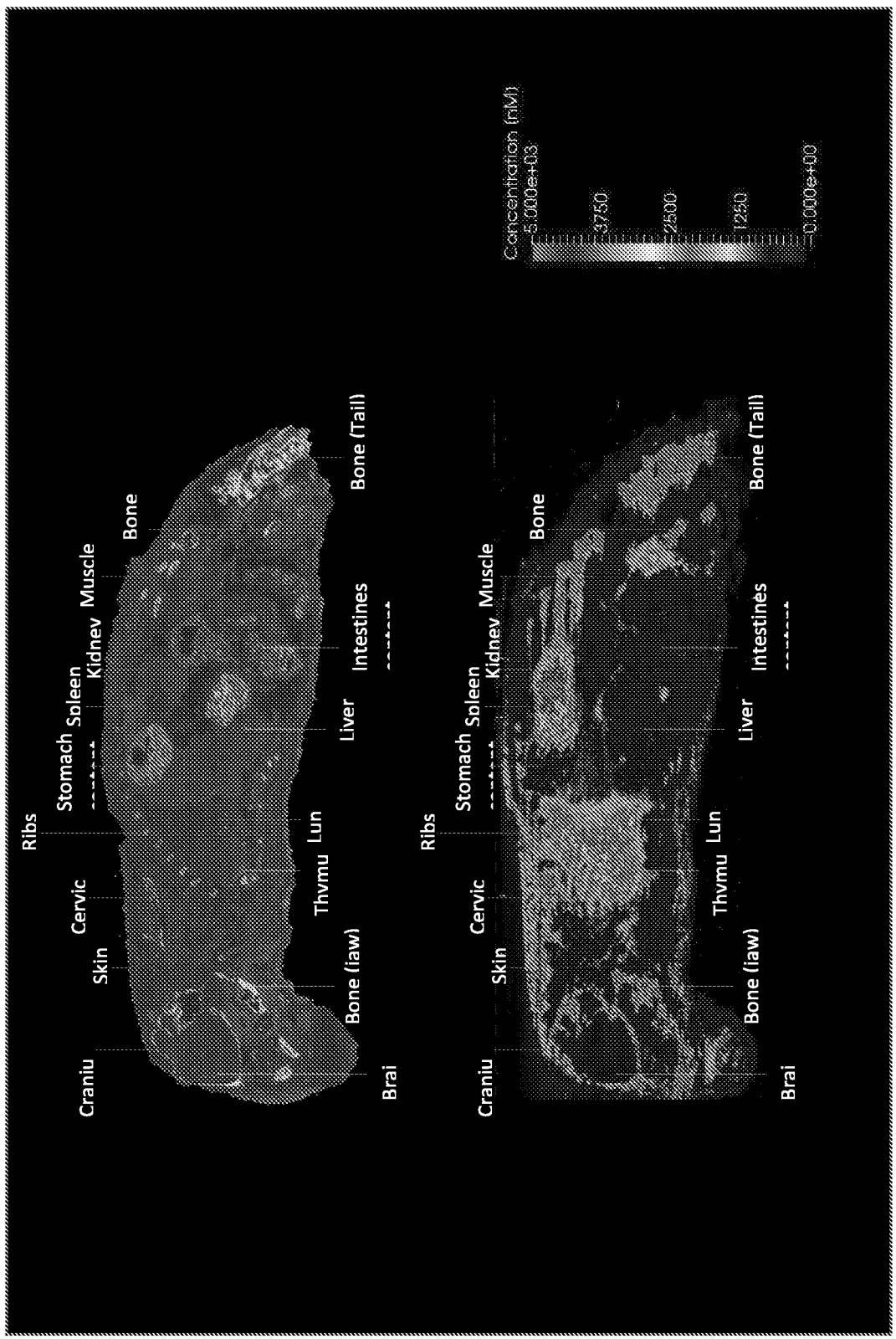
FIG. 8 shows the quantification imaging map based on the LA-ICP-MS analysis of platinum in treated mice at T45 min Section Plan 2.
Figure 9:
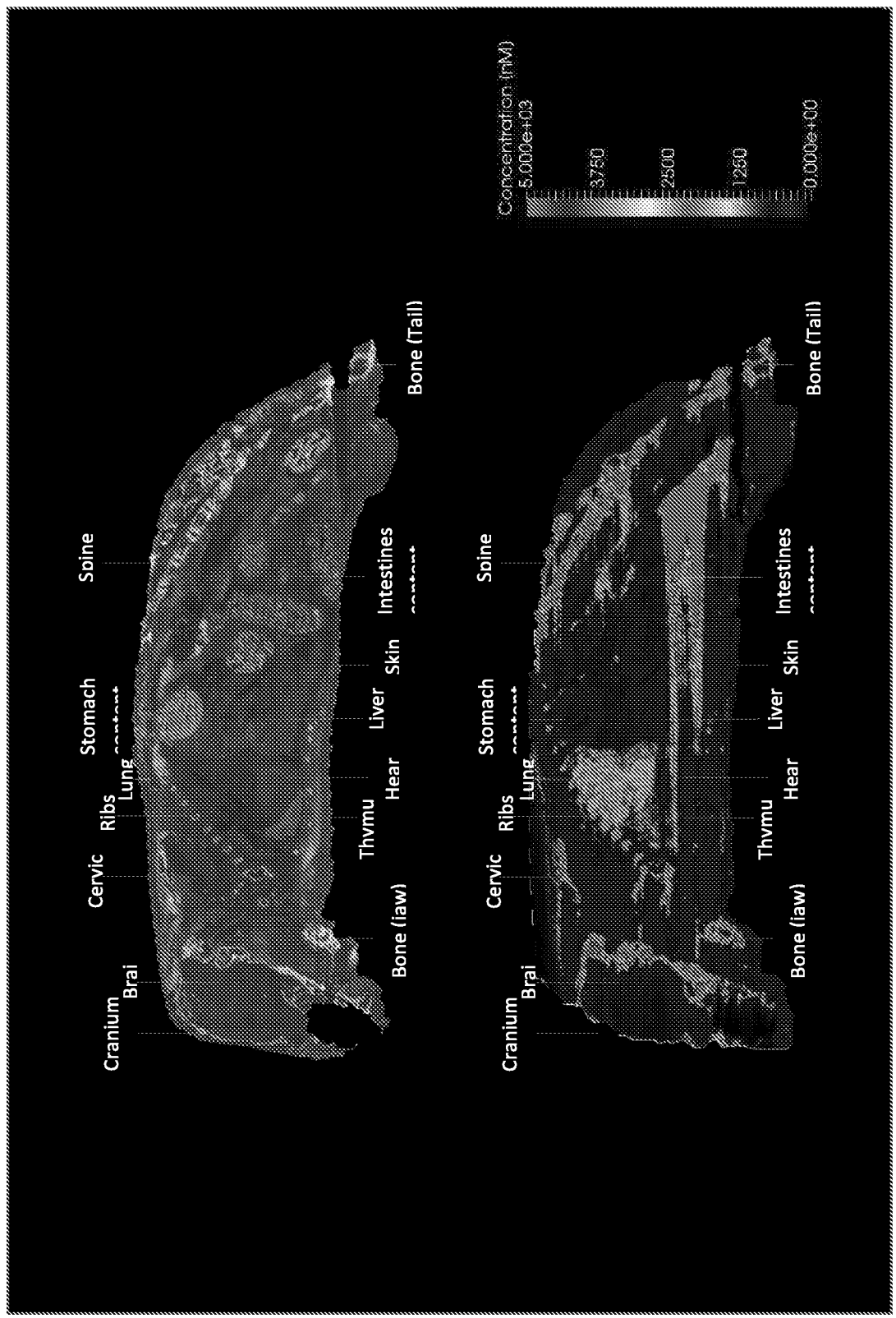
FIG. 9 shows the quantification imaging map based on the LA-ICP-MS analysis of platinum in treated mice at T45 min Section Plan 3.
Figure 10:
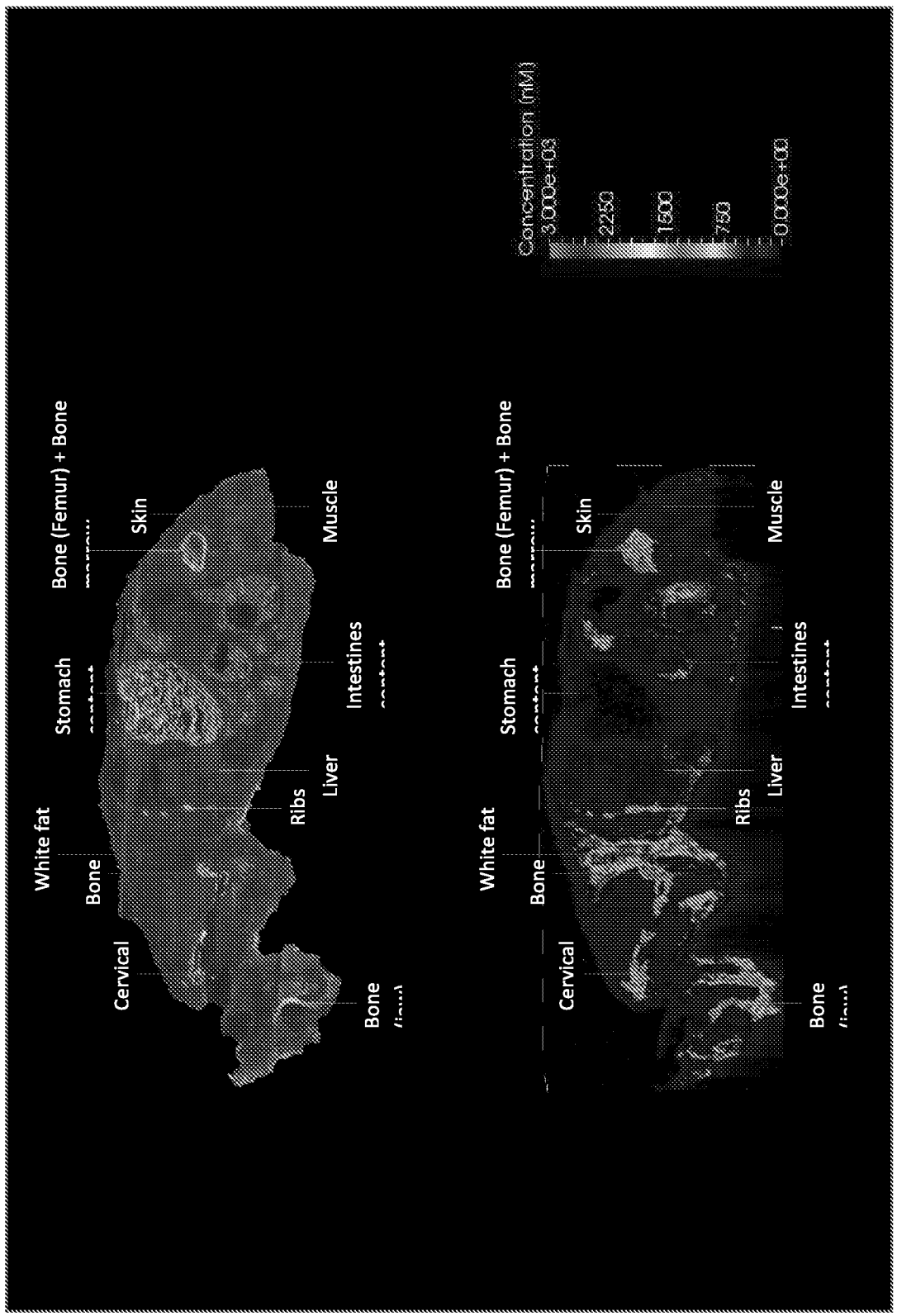
FIG. 10 shows the quantification imaging map based on the LA-ICP-MS analysis of platinum in treated mice at T24 h Section Plan 1.
Figure 11:
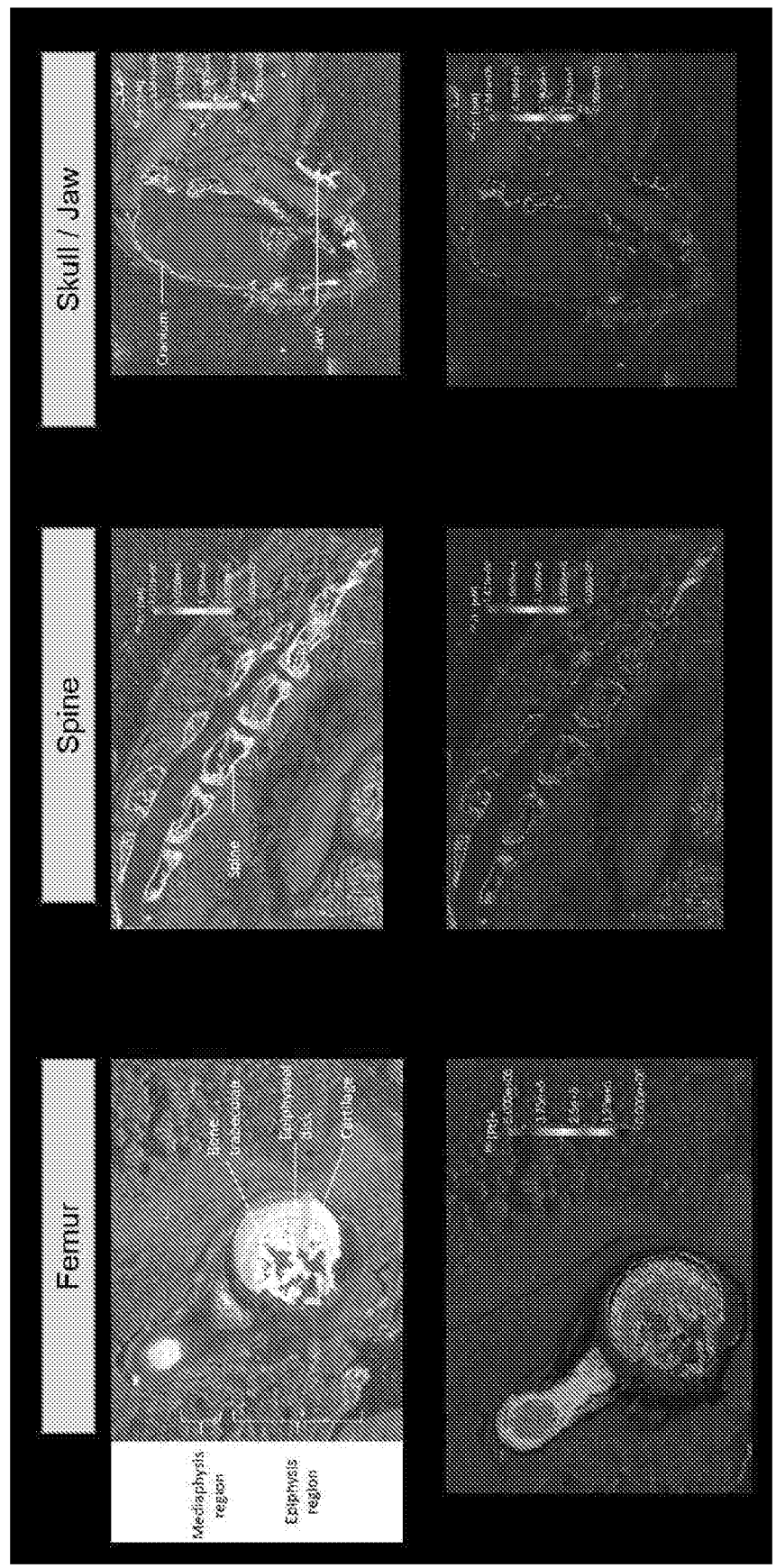
FIG. 11 shows the quantification imaging map based on the LA-ICP-MS analysis of platinum in treated mice at T45 min in bone-containing subsections.

The results on distribution and quantification from ICP-MS imaging are listed in Table 2. The ICP-MS imaging results of platinum in the T45 min mouse section plans 1, 2, and 3 are shown in FIGS. 7, 8, and 9, respectively. A cross section from the T24 hrs time point is shown in FIG. 10, and higher resolution images of different bone-containing regions from T45 min is shown in FIG. 11. Note: The "spreading" effects observed in some of the tissue sections is a washout effect of material within the ablation cell, not due to a delocalization of the platinum. This occurs on every LA-ICP-MS system for concentrated areas where the system can achieve a signal drop of 1-2 orders of magnitude every 50 ms.

In the control sample, very little Pt (~100 nM) was detected, with low levels of Pt detected in the intestines and stomach. At T=45 min, the Pt was most prominently concentrated in bones (>200 μM), although significant amounts were also detected in other locations, such as the kidney, lung, and liver. At T=24 hrs, the highest Pt signal came from bone tissue, albeit at lower concentrations (<3 μM) than observed at T45 min.

TABLE 2

Distribution and Quantification Results by ICP-MS Imaging

|  | Section Plane | ROI | Spatial Resolution (μm) | C (μM) | C (μg/g)* |
|---|---|---|---|---|---|
| Low Spatial Resolution | 1 | Femur | 150 | 74.5 | 14.5 |
|  |  | Kidney |  | 143.8 | 28.1 |
|  |  | Ribs |  | 63.8 | 12.4 |
|  |  | Spleen |  | 8.7 | 1.7 |
|  |  | White Fat |  | 10.9 | 2.1 |
|  | 2 | Brain |  | 2.3 | 0.4 |
|  |  | I contents |  | 5.8 | 1.1 |
|  |  | Jaw |  | 36.6 | 7.1 |
|  |  | Kidney |  | 49.3 | 9.6 |
|  |  | Liver |  | 9.4 | 1.8 |
|  |  | Lung |  | 25.0 | 4.9 |
|  |  | Skin |  | 14.8 | 2.9 |
|  |  | Spine |  | 66.6 | 13.0 |
|  | 3 | Cranium |  | 26.9 | 5.2 |
|  |  | Heart |  | 8.8 | 1.7 |
|  |  | Spine |  | 53.6 | 10.5 |
|  |  | Thymus |  | 8.3 | 1.6 |
|  |  | Unknown |  | 975.6 | 190.3 |
|  |  | Brain |  | 2.2 | 0.4 |
| High Spatial Resolution | 1 | Kidney | 50 | 219.8 | 42.9 |
|  |  | Epiphyseal disk | 20 | 244.6 | 47.7 |
|  | 2 | Liver | 40 | 12.5 | 2.4 |
|  |  | Lung | 50 | 30.0 | 5.9 |
|  |  | Ribs | 50 | 85.5 | 16.7 |
|  | 3 | Brain | 50 | 1.8 | 0.4 |
|  |  | Cranium | 50 | 135.3 | 26.4 |
|  |  | Jaw | 50 | 69.9 | 13.6 |
|  |  | Spine | 30 | 257.0 | 50.1 |

Conclusions

Among other target tissues, (R,R)-pyrodach-2 (or (R,R)-pyrodach-2 derived Pt) clearly concentrates in bone compartments at very high concentrations over a long period of time, which we postulated is due to the pyrophosphate content of the molecule. In in vitro experiments where (R,R)-pyrodach-2 has been tested on several different cancerous cell lines, including leukemia and multiple myeloma cell lines resistant to lenalidomide, dexamethasone, and/or bortezomib, typically low micromolar concentrations are sufficient to kill cancer cells. Thus, these bone tissues are exposed to (R,R)-pyrodach-2 (or derived Pt) at concentrations much higher than what is normally needed to induce cancer cell death. This perhaps explains the high activity of (R,R)-pyrodach-2 in the multiple myeloma Vk*MYC mouse model, and suggests that (R,R)-pyrodach-2 would be particularly effective at combating cancers that are localized to the bone.

Example 4

Clinical Activity of R,R-pyrodach-2 in Patients With Metastatic Castration Resistant Prostate Cancer (mCRPC)

Decline in Prostate-Specific Antigen (PSA)

Background

In an ongoing phase I solid tumor dose escalation study, R,R-pyrodach-2 (PT-112) was given to a 63-year-old patient with mCRPC at a dose of 200 mg/m$^2$, dosed on days 1, 8, and 15 of a 28 day cycle.

Results

Figure 12:
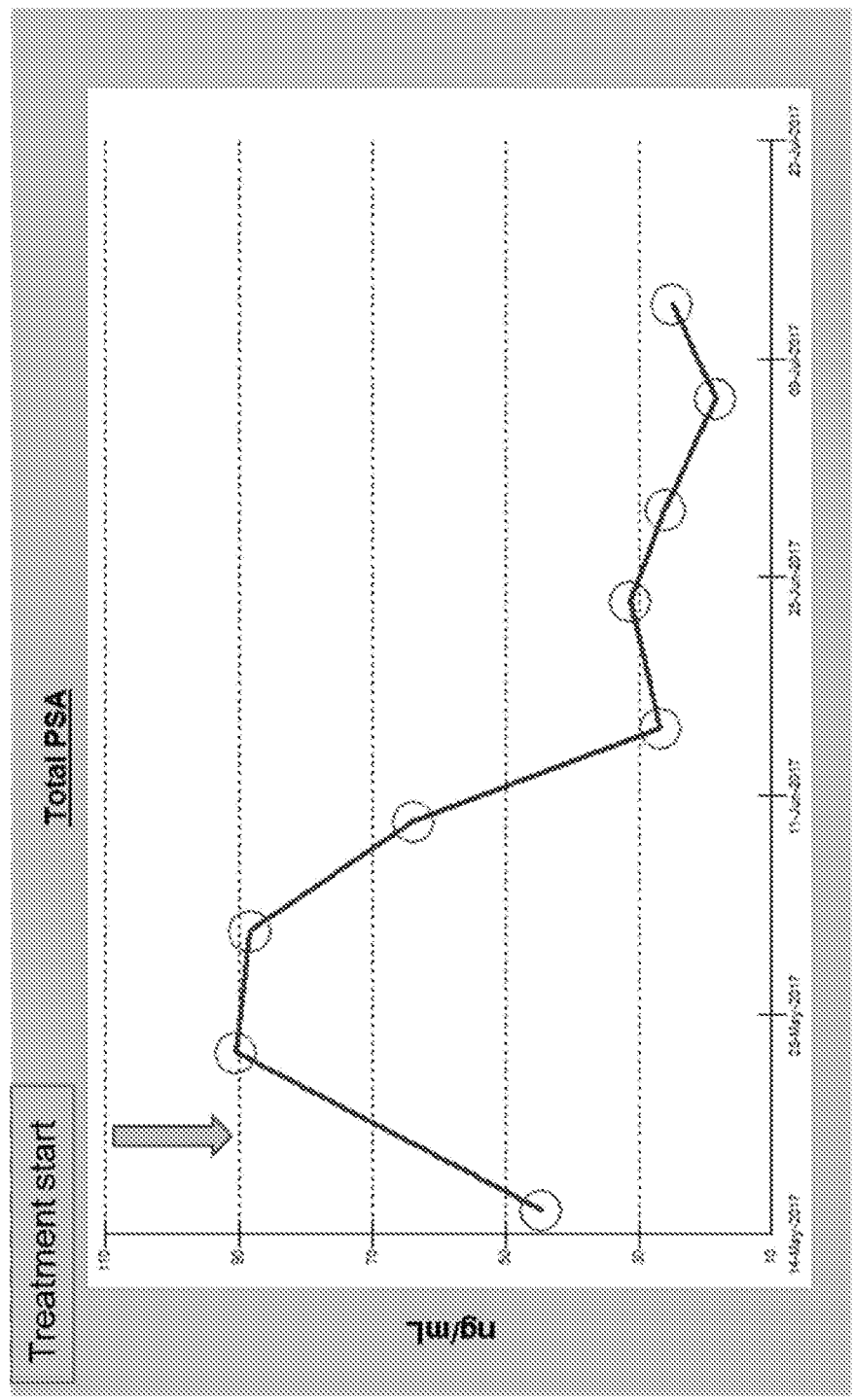
FIG. 12 shows (R,R)-pyrodach-2 induced reductions in PSA in a patient with mCRPC.

This heavily pre-treated, metastatic patient experienced an acute decline in PSA after the treatment started. After less than a full cycle of treatment, the drop in PSA was approximately 80%. PSA measurements from this patient are shown in FIG. 12.

Conclusions

R,R-pyrodach-2 is highly active in this patient with mCRPC. The activity may be explained in part by high concentration of drug at sites of metastatic bone disease.

Decline in Serum Alkaline Phosphatase Levels

Background

In an ongoing phase I solid tumor dose escalation study, R,R-pyrodach-2 (PT-112) was given to a 71-year-old patient with mCRPC at a dose of 250 mg/m$^2$, dosed on days 1, 8, and 15 of a 28 day cycle. The patient enrolled in the study with elevated serum alkaline phosphatase levels, a sign of metastatic bone disease.

Results

Figure 13:
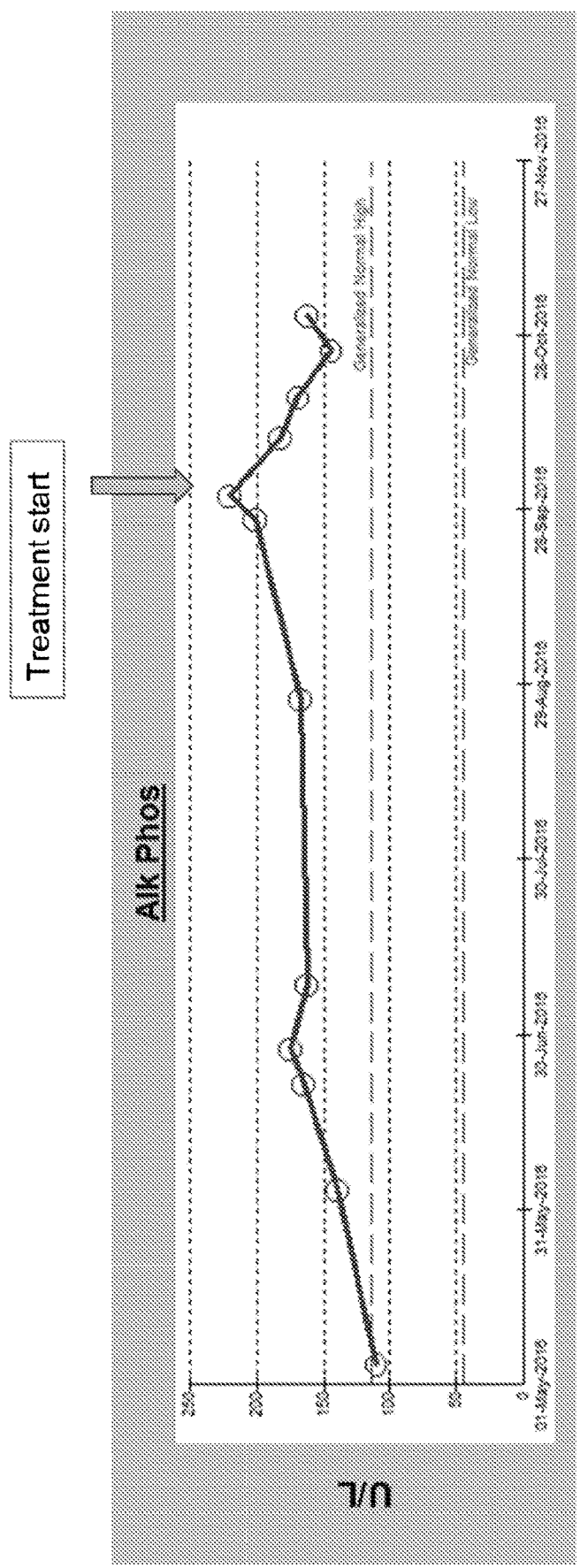
FIG. 13 shows (R,R)-pyrodach-2 induced reductions in serum alkaline phosphatase in a patient with mCRPC.

Upon treatment start, the patient experienced a rapid decline in serum alkaline phosphatase levels, a sign of anticancer drug activity at cancerous bone lesions. Alkaline phosphatase measurements from this patient are shown in FIG. 13. These measurements were fractionated to validate the proportion of the result emanating from bone (vs. liver). The bone proportion represented the vast majority of the result, validating the relationship to the metastatic bone disease in this patient.

Conclusions

R,R-pyrodach-2 was highly active in this patient with mCRPC, as indicated by acute declines in serum alkaline phosphatase levels. This example serves as additional evidence of the activity of R,R-pyrodach-2 on cancers residing in or on bone.

Example 5

Clinical Activity of R,R-pyrodach-2 at Site of Bone Disease in Patient With Metastatic Basal Cell Carcinoma (mBCC)

Background

In an ongoing phase I solid tumor dose escalation study, R,R-pyrodach-2 (PT-112) was given to a 63-year-old patient with mBCC at a dose of 150 mg/m$^2$, dosed on days 1, 8, and 15 of a 28 day cycle.

Results

Figure 14:
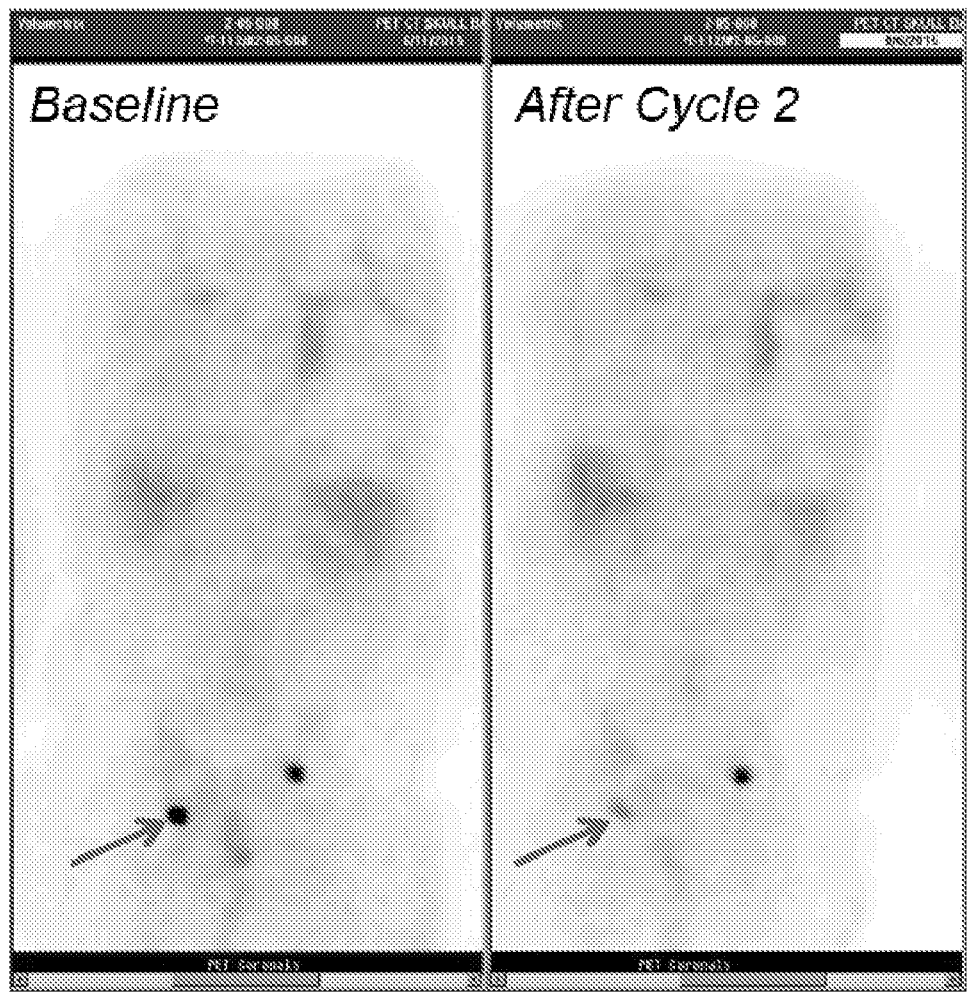
FIG. 14 shows (R,R)-pyrodach-2 induced reductions in SUV signal at the site of metastatic bone disease in a patient with metastatic basal cell carcinoma.

After two cycles of treatment, positron emission tomography (PET) imaging revealed a marked reduction in signal intensity at a metastatic bone site on the right side of the sacrum, as indicated by a decline in standard update values (SUVs) from 10.2 at baseline to 3.8 after the two treatment cycles. The baseline and post-cycle two PET images are down in FIG. 14.

Conclusions

R,R-pyrodach-2 demonstrated high activity at this site of bone disease, which supports the argument that R,R-pyrodach-2 is particularly potent and active in treating cancers residing in or on bone tissue. Additionally, while the maximum tolerated dose (MTD) has yet to be determined in this trial, the dose of 150 mg/m$^2$ is well below the highest dose deemed to be safe of 360 mg/m$^2$, indicating that these anticancer effects at sites of bone disease can occur at doses that are very well tolerated.

The foregoing non-limiting examples and embodiments are described to illustrate certain aspects of the present invention. Those skilled in the art will understand that various changes or modifications may be made without departing from the spirit and scope of the invention. All references mentioned herein are incorporated by reference in their entirety.

What is claimed is:

1. A method for treating a subject having a bone or blood cancer, or a cancer that metastasizes to bone, comprising administering to the subject a therapeutically effective amount of a phosphaplatin compound having a structure of formula II:

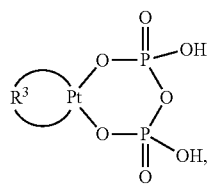

(II)

or a pharmaceutically acceptable salt thereof, wherein $R^3$ is selected from the group consisting of substituted or unsubstituted aliphatic diamines and substituted or unsubstituted aromatic diamines.

2. The method of claim 1, wherein $R^3$ is selected from the group consisting of 1,2-ethylenediamine and cyclohexane-1,2-diamine.

3. The method of claim 1, wherein the phosphaplatin compound is selected from the group consisting of:

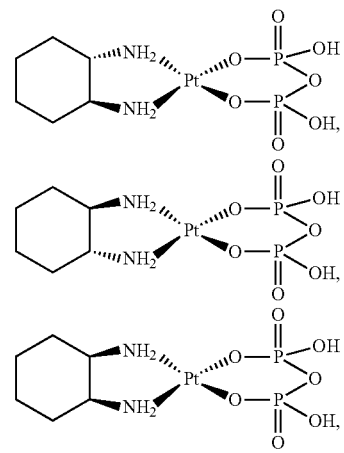

pharmaceutically acceptable salts, and mixtures thereof.

4. The method of claim 1, wherein the phosphaplatin compound is (R,R)-1,2-cyclohexanediamine-(dihydrogen pyrophosphato) platinum(II) (or "PT-112"), or a pharmaceutically acceptable salt thereof.

5. A method for treating a subject having a bone or blood cancer, or a cancer that metastasizes to bone, comprising administering to the subject a therapeutically effective amount of a phosphaplatin compound having a structure of formula III or IV:

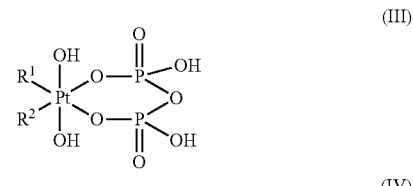

(III)

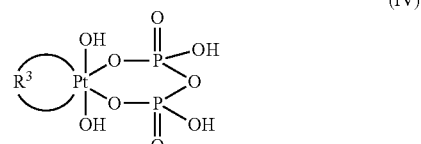

(IV)

or a pharmaceutically acceptable salt thereof, wherein $R^1$ and $R^2$ are each independently selected from the group consisting of NH$_3$, substituted or unsubstituted aliphatic amines, and substituted or unsubstituted aromatic amines; and wherein $R^3$ is selected from the group consisting of substituted or unsubstituted aliphatic diamines and substituted or unsubstituted aromatic diamines.

6. The method of claim 5, wherein $R^1$ and $R^2$ are each independently selected from the group consisting of NH$_3$, methyl amine, ethyl amine, propyl amine, isopropyl amine, butyl amine, cyclohexane amine, aniline, pyridine, and substituted pyridine; and R³ is selected from the group consisting of 1,2-ethylenediamine and cyclohexane-1,2-diamine.

7. The method of claim 5, wherein the monomeric platinum (IV) pyrophosphate complex has a formula (IV), wherein R³ is 1,2-ethylene-diamine or cyclohexane-1,2-diamine.

8. The method of claim 5, wherein the phosphaplatin compound is selected from the group consisting of:

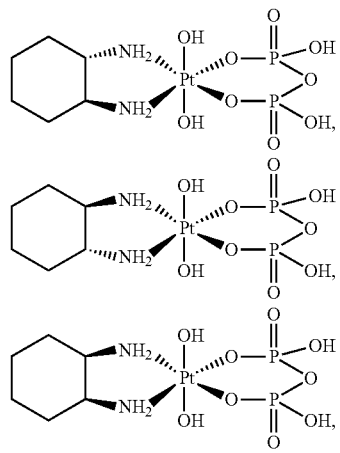

pharmaceutically acceptable salts, and mixtures thereof.

9. The method of claim 1, wherein the administering comprises intravenous or intraperitoneal injection.

10. The method of claim 1, wherein the dose of pyrophosphate platinum complex is in the range of from about 1 mg and to about 200 mg/Kg based on body weight of the subject.

11. The method of claim 1, wherein the bone or blood cancer is selected from the group consisting of osteosarcoma, chondrosarcoma, Ewing tumor, malignant fibrous histiocytoma (MFH), fibrosarcoma, giant cell tumor, chordoma, spindle cell sarcomas, multiple myeloma, non-Hodgkin lymphoma, Hodgkin lymphoma, leukemia, childhood acute myelogenous leukemia (AML), chronic myelomonocytic leukaemia (CMML), hairy cell leukaemia, juvenile myelomonocytic leukaemia (JMML), myelodysplastic syndromes, myelofibrosis, myeloproliferative neoplasms, polycythaemia vera, and thrombocythaemia.

12. The method of claim 11, wherein the bone or blood cancer is selected from the group consisting of osteosarcoma, chondrosarcoma, Ewing tumor, malignant fibrous histiocytoma (MFH), fibrosarcoma, giant cell tumor, chordoma, spindle cell sarcomas, multiple myeloma, non-Hodgkin lymphoma, Hodgkin lymphoma, and leukemia.

13. The method of claim 1, in conjunction with administering to the subject a second anti-cancer agent.

14. The method of claim 13, wherein the second anti-cancer agent is selected from the group consisting of alkylating agents, glucocorticoids, immunomodulatory drugs (IMiDs) and proteasome inhibitors.

15. Use of A method of treating a bone or blood cancer or a cancer that metastasizes to bones, comprising administering to a subject in need of such treatment a therapeutically effective amount of (R,R)-1,2-cyclohexanediamine-(dihydrogen pyrophosphate) platinum(II) (or "PT-112"), or a pharmaceutically acceptable salt thereof, wherein the bone or blood cancer is selected from the group consisting of osteosarcoma, chondrosarcoma, Ewing tumor, malignant fibrous histiocytoma (MFH), fibrosarcoma, giant cell tumor, chordoma, spindle cell sarcomas, multiple myeloma, non-Hodgkin lymphoma, Hodgkin lymphoma, leukemia, childhood acute myelogenous leukemia (AML), chronic myelomonocytic leukaemia (CMML), hairy cell leukaemia, juvenile myelomonocytic leukaemia (JMML), myelodysplastic syndromes, myelofibrosis, myeloproliferative neoplasms, polycythaemia vera, and thrombocythaemia.

* * * * *